(12) United States Patent
Eyjolfsson

(10) Patent No.: US 7,589,064 B2
(45) Date of Patent: Sep. 15, 2009

(54) FORMULATIONS OF RAMIPRIL

(75) Inventor: Reynir Eyjolfsson, Hafnarfjordur (IS)

(73) Assignee: Actavis Group hf. (IS)

( * ) Notice: Subject to any disclaimer, the term of this patent is extended or adjusted under 35 U.S.C. 154(b) by 0 days.

(21) Appl. No.: 11/777,849

(22) Filed: Jul. 13, 2007

(65) Prior Publication Data

US 2007/0254030 A1 Nov. 1, 2007

Related U.S. Application Data

(63) Continuation of application No. 10/593,627, filed as application No. PCT/IS2005/000008 on Mar. 23, 2005.

(30) Foreign Application Priority Data

Mar. 24, 2004 (IS) .......................................... 7196
Mar. 23, 2005 (IS) .......................................... 7772

(51) Int. Cl.
*A61K 38/00* (2006.01)
(52) U.S. Cl. ....................................................... 514/16
(58) Field of Classification Search .................... 514/16
See application file for complete search history.

(56) References Cited

U.S. PATENT DOCUMENTS

| | | | |
|---|---|---|---|
| 4,727,160 A | 2/1988 | Teetz et al. | |
| 4,743,450 A | 5/1988 | Harris et al. | |
| 4,830,853 A | 5/1989 | Murthy et al. | |
| 5,151,433 A | 9/1992 | Fulbreth et al. | |
| 5,256,687 A | 10/1993 | Becker et al. | |
| 5,686,451 A | 11/1997 | Kristianson et al. | |
| 5,753,254 A | 5/1998 | Khan et al. | |
| 6,096,779 A * | 8/2000 | Chikaraishi et al. | 514/429 |
| 6,217,907 B1 * | 4/2001 | Hunter et al. | 424/489 |
| 6,303,147 B1 | 10/2001 | Gilis | |
| 6,458,384 B2 | 10/2002 | Jaenicke et al. | |
| 6,555,551 B1 | 4/2003 | Spireas | |
| 6,576,256 B2 | 6/2003 | Liang et al. | |
| 6,667,060 B1 | 12/2003 | Vandecruys et al. | |
| 6,844,361 B2 | 1/2005 | Linz et al. | |
| 6,869,963 B2 | 3/2005 | Patel et al. | |
| 2003/0027837 A1 | 2/2003 | Sherman | |
| 2003/0049314 A1 | 3/2003 | Liang et al. | |
| 2003/0148960 A1 * | 8/2003 | MacLaughlan et al. | 514/16 |
| 2003/0215526 A1 * | 11/2003 | Stofik et al. | 424/715 |
| 2003/0225124 A1 | 12/2003 | Spireas | |
| 2004/0137054 A1 | 7/2004 | Hager et al. | |
| 2004/0157911 A1 | 8/2004 | Spireas | |
| 2004/0157928 A1 | 8/2004 | Kim et al. | |
| 2004/0171669 A1 | 9/2004 | Chenevier | |
| 2005/0009806 A1 | 1/2005 | Patel et al. | |
| 2005/0069586 A1 | 3/2005 | Hrakovsky et al. | |
| 2005/0106237 A1 | 5/2005 | Wuthrich et al. | |
| 2005/0106251 A1 | 5/2005 | Langridge et al. | |
| 2005/0118259 A1 | 6/2005 | Eyjolfsson | |
| 2005/0142196 A1 | 6/2005 | Patel et al. | |
| 2005/0169981 A1 | 8/2005 | Sherman | |
| 2005/0186274 A1 | 8/2005 | Kohlrausch | |
| 2005/0192315 A1 | 9/2005 | Jansson et al. | |
| 2005/0202081 A1 | 9/2005 | Bahl et al. | |
| 2006/0018965 A1 | 1/2006 | Moodley et al. | |
| 2006/0034937 A1 | 2/2006 | Patel | |
| 2006/0045911 A1 | 3/2006 | Dharmadhikari et al. | |
| 2006/0134213 A1 | 6/2006 | Wilson et al. | |
| 2006/0159742 A1 | 7/2006 | Wilson et al. | |
| 2006/0160736 A1 | 7/2006 | Nadler | |
| 2006/0177498 A1 | 8/2006 | Bharatrajan et al. | |
| 2006/0188568 A1 | 8/2006 | Bhamare et al. | |
| 2007/0053975 A1 | 3/2007 | Harrison et al. | |
| 2007/0098782 A1 | 5/2007 | Harrison et al. | |
| 2007/0259941 A1 | 11/2007 | Harrison et al. | |
| 2008/0108687 A1 | 5/2008 | Harrison et al. | |
| 2008/0108688 A1 | 5/2008 | Harrison et al. | |
| 2008/0234353 A1 | 9/2008 | Eyjolfsson | |

FOREIGN PATENT DOCUMENTS

| | | |
|---|---|---|
| EP | 0 215 357 A2 | 3/1987 |
| EP | 0 317 878 B1 | 4/1992 |
| EP | 0 280 999 B1 | 1/1993 |
| GB | 2 394 660 A | 5/2004 |
| GB | 2 411 355 A | 8/2005 |
| WO | WO 93/17685 A1 | 9/1993 |
| WO | WO 96/31197 A1 | 10/1996 |
| WO | WO 98/10753 A1 | 3/1998 |
| WO | WO 02/11709 A2 | 2/2002 |
| WO | WO 03/028707 A1 | 4/2003 |

(Continued)

OTHER PUBLICATIONS

Kristianson et al., Combinations of ACE Inhibitores and Diuretics, Sep. 16, 1993, International Application Published Under the PCT, WO 93/17685 (See IDS for copy).*
English language translation of EP 0 215 357, Patents Form No. 54/77, Filing of Translation of European Patent (UK) Under Section 77(6)(a), translated in 1992.
Office Action mailed Jan. 22, 2007 in U.S. Appl. No. 11/509,032, Harrison, P., et al., filed Aug. 24, 2006.
Amendment and Reply Under 37 C.F.R. § 1.111 filed Apr. 23, 2007 in U.S. Appl. No. 11/509,032, Harrison, P., et al., filed Aug. 24, 2006.
Office Action mailed Feb. 12, 2007 in U.S. Appl. No. 11/508,916, Harrison, P., et al., filed Aug. 24, 2006.
Amendment and Reply Under 37 C.F.R. § 1.111 filed May 11, 2007 in U.S. Appl. No. 11/508,916, Harrison, P., et al., filed Aug. 24, 2006.
Office Action mailed Jul. 25, 2007 in U.S. Appl. No. 11/508,916, Harrison, P., et al., filed Aug. 24, 2006.

(Continued)

*Primary Examiner*—Johann R Richter
*Assistant Examiner*—Ali Soroush
(74) *Attorney, Agent, or Firm*—Sterne, Kessler, Goldstein & Fox P.L.L.C.

(57) ABSTRACT

The present invention relates to stable tablet formulations of ramipril, optionally in combination with a diuretic.

14 Claims, No Drawings

FOREIGN PATENT DOCUMENTS

| WO | WO 03/059388 A1 | 7/2003 |
| --- | --- | --- |
| WO | WO 03/063834 A1 | 8/2003 |
| WO | WO 03/075842 A2 | 9/2003 |
| WO | WO 03/092729 A1 | 11/2003 |
| WO | WO 2004/056360 A1 | 7/2004 |
| WO | WO 2004/064809 A1 | 8/2004 |
| WO | WO 2005/002548 A1 | 1/2005 |
| WO | WO 2005/007130 A1 | 1/2005 |
| WO | WO 2005/041940 A1 | 5/2005 |
| WO | WO 2005/067887 A2 | 7/2005 |
| WO | WO 2005/079748 A2 | 9/2005 |
| WO | WO 2005/079762 A1 | 9/2005 |
| WO | WO 2005/082420 A1 | 9/2005 |

OTHER PUBLICATIONS

Amendment and Reply Under 37 C.F.R. § 1.114 filed Sep. 25, 2007 in U.S. Appl. No. 11/508,916, Harrison, P., et al., filed Aug. 24, 2006.

Office Action mailed Jan. 31, 2008 in U.S. Appl. No. 11/508,916, Harrison, P., et al., filed Aug. 24, 2006.

Office Action mailed Apr. 2, 2008 in U.S. Appl. No. 11/976,865, Harrison, P., et al., filed Oct. 29, 2007.

Altace® Patient Information Leaflet, "Altace® Capsules," Monarch Pharmaceuticals, Inc., 8 pages (Sep. 2005).

Bastin, R.J., et al, "Salt Selection and Optimisation Procedures for Pharmaceutical New Chemical Entities," *Organic Process Research & Development* 4:427-435, American Chemical Society (2000).

Eyjolfsson, R., "Calcium sulphate dihydrate: an useful excipient for tablets containing labile actives," *Pharmazie* 59:725-726, Govi-Verlag Pharmazeutischer Verlag GmbH (2004).

Kibbe, A.H., ed., "Calcium sulfate" in: Handbook of Pharmaceutical Excipients, American Pharmaceutical Association, Washington, D.C., pp. 73-76 (2000).

Rhoades, K.R., "Prescribed Medications and OTCs: Interactions and Timing Issues," *Diabetes Spectrum* 15:256-261, American Diabetes Association (2002).

Search Report for U.K. Application No. GB 0522047.0, UK Patent Office (conducted on Mar. 27, 2006).

STNEasyDatabase, Accession No. 1989-158982, Derwent WPI English language abstract of EP 0 317 878 B1 (listed on accompanying PTO/SB/08A as document FP9).

English language abstract of WO 2002/11709 A2, Derwent Accession No. 2002-241700, 5 pages (Document FP13 listed on accompanying PTO/SB/08A).

STNEasyDatabase, Accession No. 2003:892642, Derwent WPI English language abstract of WO 2003/092729 A1 (listed on accompanying PTO/SB/08A as document FP14).

English language abstract of IN 200301115, Derwent Accession No. 2006-112723, 2 pages.

English language abstract of DE 4334936 C1, 1 page (published Jun. 22, 1995).

English language abstract of CN 1524523 A, Derwent Accession No. 2004-797500, 2 pages.

International Search Report for International Patent Appl. No. PCT/IS2005/000008, mailed Sep. 16, 2005, European Patent Office, The Netherlands.

WPI Database, Accession No. 2006-112723, English language abstract of IN 1115/MUM/2003.

Office Action mailed Jul. 26, 2007 in U.S. Appl. No. 11/509,032, Harrison, P., et al., filed Aug. 24, 2006.

Amendment and Reply Under 37 C.F.R. § 1.114 filed Sep. 25, 2007 in U.S. Appl. No. 11/509,032, Harrison, P., et al., filed Aug. 24, 2006.

Office Action mailed Nov. 30, 2007 in U.S. Appl. No. 11/509,032, Harrison, P., et al., filed Aug. 24, 2006.

Amendment and Reply Under 37 C.F.R. § 1.111 filed May 30, 2008 in U.S. Appl. No. 11/509,032, Harrison, P., et al., filed Aug. 24, 2006.

Office Action mailed Aug. 13, 2008 in U.S. Appl. No. 11/509,032, Harrison, P., et al., filed Aug. 24, 2006.

Office Action mailed Nov. 29, 2007 in U.S. Appl. No. 11/508,916, Harrison, P., et al., filed Aug. 24, 2006.

Amendment and Statement of Substance of Interview Under 37 C.F.R. § 1.111 filed Nov. 30, 2007 in U.S. Appl. No. 11/508,916, Harrison, P., et al., filed Aug. 24, 2006.

Amendment and Reply Under 37 C.F.R. § 1.111 filed Jul. 31, 2008 in U.S. Appl. No. 11/508,916, Harrison, P., et al., filed Aug. 24, 2006.

Office Action mailed Oct. 23, 2008 in U.S. Appl. No. 11/508,916, Harrison, P., et al., filed Aug. 24, 2006.

Amendment and Reply Under 37 C.F.R. § 1.111 filed Oct. 2, 2008 in U.S. Appl. No. 11/976,865, Harrison, P., et al., filed Oct. 29, 2007.

Office Action mailed Oct. 7, 2008 in U.S. Appl. No. 10/593,627, Eyjolfsson, R., filed Sep. 21, 2006.

Office Action mailed Dec. 19, 2008 in U.S. Appl. No. 11/976,859, Harrison, P. et al., filed Oct. 29, 2007.

Office Action mailed Jan. 8, 2009 in U.S. Appl. No. 11/976,865, Harrison, P., et al., filed Oct. 29, 2007.

\* cited by examiner

FORMULATIONS OF RAMIPRIL

FIELD OF THE INVENTION

The present invention relates to stable pharmaceutical formulations of ramipril, optionally in combination with a diuretic.

TECHNICAL BACKGROUND AND PRIOR ART

Ramipril, (2S,3aS,6aS)-1[(S)—N—[(S)-1-carboxy-3-phenylpropyl]alanyl]octahydrocyclopenta[b]pyrrole-2-carboxylic acid, 1-ethyl ester is an angiotensin converting enzyme (ACE) inhibitor. Ramipril is used for the treatment of hypertension, heart failure, stroke, myocardial infarction, diabetes and cardiovascular disease.

Ramipril and the acid form, ramiprilat, is described in EP 0 097 022 B1.

The preparation of stable pharmaceutical formulations of ramipril is complicated since it is susceptible to certain types of degradation. Ramipril can undergo cyclization via internal nucleophilic attack to form substituted diketopiperazines and also degrade via hydrolysis and oxidation.

EP 1 501 546 A1 describes stable pharmaceutical formulation for combinations of a statin and an ACE inhibitor. The problem underlying the invention is that if an ACE inhibitor is in the presence of a stabilised statin, the ACE inhibitor decomposes to such extent that even after short storage period the content of decomposition products exceeds the permissible limit of degradation. EP 1 501 546 A1 provides a formulation wherein the statin and the ACE inhibitor are separated by physiologically acceptable inert material. Calcium sulfate is mentioned as a possible inorganic filler in the formulation but it is neither claimed nor mentioned in any example. In fact all the examples are concerned with three-layer tablet, wherein the statin layer and ACE inhibitor layer are separated by a layer of microcrystalline cellulose. The combination of the ACE inhibitor with a diuretic are not mentioned.

US 2003/0215526 claims formulations of ACE inhibitor a pharmaceutical composition comprising a therapeutically effective amount of an ACE inhibitor which is susceptible to degradation or its salt; a greater than stoichiometric amount of an alkali or alkaline earth metal carbonate, relative to the amount of ACE inhibitor or its salt, and a pharmaceutically acceptable carrier. The excipient calcium sulphate is not mentioned.

EP 0 280 999 B1 describes a composition comprising ACE inhibitor (i.e. ramipril), an alkali or alkaline earth metal carbonate and saccharide wherein the ACE inhibitor is stabilized against degradation (cyclization, discoloration and hydrolysis) by means of the other mentioned ingredients. In the specifications the relevant saccharides are lactose and mannitol. Modified starch is mentioned as disintegrant in the specification.

EP 0 317 878 B1 claims a stable, compressed pharmaceutical formulation containing a compound of a defined formula (i.e. ramipril) wherein, for stabilization before compression, a compound of the formula is a) coated with a polymeric, physiologically tolerated protective coating, or b) mixed with a physiologically tolerated buffer which ensures that a pH in the weakly acidic to weakly alkaline range is set up in a pharmaceutical formulation in the presence of moisture, where sodium bicarbonate is excepted as buffer, or c) mixed with a physiologically tolerated buffer which ensures that a pH in the weakly acid to weakly alkaline range is set up in a pharmaceutical formulation in the presence of moisture, and is coated with a polymeric, physiologically tolerated protective coating, where, in the case of stabilization according to b) with alkali metal or alkaline earth metal carbonate, the formulation is free of sugar.

WO 93/17685 claims combinations of ACE inhibitors and diuretics such as hydrochlorothiazide. Sodium hydrogen carbonate, pregelatinised starch and magnesium stearate are mentioned as excipients. Calcium sulphate is not mentioned.

Compositions of ramipril and piretamide is described in EP 215 357 B1. Calcium sulfate is not mentioned in this patent.

WO 03/028707 claims a formulation containing ramipril and lactose monohydrate. Calcium sulfate is mentioned in the specification as a possible diluent. Calcium sulfate is not included any example.

SUMMARY OF THE INVENTION

In an attempt to prepare a stable tablet formulation of ramipril, it was discovered that useful formulations can be produced by the use of calcium sulphate dihydrate (e.g. Compactrol) as filler material.

Properties of calcium sulphate are described in A. H. Kibbe, Handbook of pharmaceutical excipients, 73-76, American Pharmaceutical Association, Washington, and Pharmaceutical Press, London, 2000.

Calcium sulphate dihydrate is known as an inert diluent in compressed tablets. However, it was surprising that the stability of the tablets proved to be very satisfying.

DETAILED DESCRIPTION

The invention provides a pharmaceutical formulation comprising ramipril,

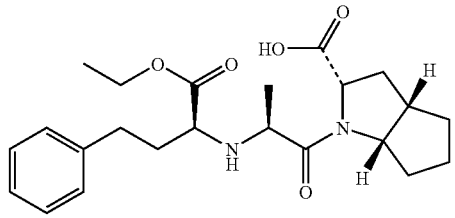

Compactrol as filling agent, and sodium hydrogen carbonate as stabilization agent.

The pharmaceutical formulation of the present invention comprises typically:

a) 0.1-5.0% w/w of ramipril;

b) 50-95% w/w of Compactrol;

c) 0.1-5.0% w/w of sodium hydrogen carbonate;

and optionally disintegrant (e.g. starch), binder and/or lubricant (e.g. sodium stearyl fumarate).

The optional disintegrant and/or binder of the formulation can be pregelatinised starch.

The formulation optionally also includes a diuretic, such as hydrochlorothiazide or piretanide.

For the tablet formulation containing 1.25 mg ramipril, the preferred amount of ramipril is 0.5-1.5% w/w, the amount of Compactrol is 85-90% w/w, the amount of sodium hydrogen carbonate is 0.5-1.5% w/w, the amount of starch pregelatinised is 7-13% w/w and the amount of sodium stearyl fumarate is 0.5-1.5% w/w.

For the tablet formulation containing 2.5 mg, 5 mg and 10 mg ramipril, the preferred amount of ramipril is 1.4-2.5% w/w, the amount of Compactrol is 78-95% w/w, the amount of sodium hydrogen carbonate is 1.4-2.5% w/w, the amount of starch pregelatinised is 7-13% w/w and the amount of sodium stearyl fumarate is 0.5-1.5% w/w.

For the tablet formulation containing 2.5 mg ramipril/12.5 mg hydrochlorothiazide and 5 mg ramipril/25 mg hydrochlorothiazide, preferred amount of ramipril is 1.4-2.5% w/w, the amount of hydrochlorothiazide is 8.5-10.5% w/w, the amount of Compactrol is 65-75% w/w, the amount of sodium hydrogen carbonate is 1.0-2.5% w/w, the amount of starch pregelatinised is 12-18% w/w and the amount of sodium stearyl fumarate is 0.5-1.5% w/w.

For the tablet formulation containing 5 mg ramipril and 6 mg piretanide, the preferred amount of ramipril is 1.5-2.5% w/w, the amount of piretanide is 1.8-3.0% w/w, the amount of Compactrol is 65-85% w/w, the amount of sodium hydrogen carbonate is 3.0-5.0% w/w, the amount of starch pregelatinised is 10-20% w/w and the amount of sodium stearyl fumarate is 0.5-1.5% w/w.

Since ramipril is susceptible to certain types of degradation, there are several impurities formed during the manufacturing process and storing of the tablet. It is of high importance to minimize this degradation. The strength of different excipients was adjusted until a useful formulation was found.

There are certain criterias that these compounds are not allowed to exceed. The present formulation has proved to be stable.

Ramipril diketopiperazine is one of the compounds formed via degradation. The present formulation proved to be especially stable with regard to formation of the diketopiperazine.

EXAMPLES

The following example is merely illustrative of the present invention and it should not be considered as limiting the scope of the invention.

Example 1

Formulation for 1.25 mg Ramipril Tablets

| | |
|---|---|
| Ramipril | 0.96% |
| Compactrol | 87.08% w/w |
| Sodium hydrogen carbonate | 0.96% w/w |
| Starch pregelatinised | 10.00% w/w |
| Sodium stearyl fumarate | 1.00% w/w |

Example 2

Formulation for 2.5 mg, 5 mg and 10 mg Ramipril Tablets

| | |
|---|---|
| Ramipril | 1.9% w/w |
| Compactrol | 85.2% w/w |
| Sodium hydrogen carbonate | 1.9% w/w |
| Starch pregelatinised | 10.0% w/w |
| Sodium stearyl fumarate | 1.0% w/w |

Example 3

Formulation for 2.5/12.5 mg and 5/25 mg Ramipril Hydrochlorothiazide (HCT) Tablets

| | |
|---|---|
| Ramipril | 1.9% w/w |
| Hydrochlorothiazide | 9.6% w/w |
| Compactrol | 70.5% w/w |
| Sodium hydrogen carbonate | 1.9% w/w |
| Starch pregelatinised | 15.0% w/w |
| Sodium stearyl fumarate | 1.0% w/w |

Example 4

Formulation for 5/6 mg Ramipril Piretanide Tablets

| | |
|---|---|
| Ramipril | 1.9% w/w |
| Piretanide | 2.3% w/w |
| Compactrol | 76% w/w |
| Sodium hydrogen carbonate | 3.7% w/w |
| Starch pregelatinised | 15% w/w |
| Sodium stearyl fumarate | 1% w/w |

Example 5

Stability of 5 mg and 10 mg tablets prepared in Example 2 and of marketed preparation were tested at 40° C. and 75% relative humidity (RH) for six months. Conversion of ramipril into ramipril diketopiperazine was assayed and measured as relative amount of initial amount of ramipril.

| | Assay | Ramipril diketopiperazine |
|---|---|---|
| | 5 mg | |
| Tablets from Ex. 2 | 4.0% | 0.478-1.06% |
| Marketed prepn**. | 4.0% | 2.77% |
| | 10 mg | |
| Tablets from Ex. 2 | 4.0% | 0.471-0.806% |
| Marketed prepn**. | 4.0% | 2.27% |

**Ramitab ™ ramipril 5 and 10 mg tablets

The example demonstrates a very good stability with regard to ramipril diketopiperazine formation.

The invention claimed is:

1. A tablet formulation comprising:
   a) 1.25 mg ramipril, wherein the amount of ramipril is 0.5-1.5% w/w,
   b) 85-90% w/w of calcium sulphate dihydrate,
   c) 0.5-1.5% w/w of sodium hydrogen carbonate,
   d) 7-13% w/w starch pregelatinised, and
   e) 0.5-1.5% w/w sodium stearyl fumarate.

2. The tablet formulation of claim 1, further comprising a diuretic.

3. The tablet formulation of claim 2, wherein the diuretic is hydrochiorothiazide.

4. The tablet formulation of claim 2, wherein the diuretic is piretanide.

5. A tablet formulation comprising:
   (a) 2.5 mg, 5 mg or 10 mg ramipril, wherein the amount of ramipril is 1.4-2.5% w/w,
   (b) 78-95% w/w calcium sulphate dihydrate,
   (c) 1.4-2.5% w/w sodium hydrogen carbonate,
   (d) 7-13% w/w starch pregelatinised, and
   (e) 0.5-1.5% w/w sodium stearyl fumarate.

6. A tablet formulation comprising:
(a) 2.5 mg ramipril/12.5 mg hydrochlorothiazide or 5 mg ramipril/25 mg hydrochlorothiazide, wherein the amount of ramipril is 1.4-2.5% w/w,
(b) 8.5-10.5% w/w hydrochlorothiazide,
(c) 65-75% w/w calcium sulphate dihydrate,
(d) 1.0-2.5% w/w sodium hydrogen carbonate,
(e) 12-18% w/w starch pregelatinised, and
(f) 0.5-1.5% w/w sodium stearyl fumarate.

7. A tablet formulation comprising:
(a) 5 mg ramipril and 6 mg piretanide, wherein the amount of ramipril is 1.5-2.5% w/w and the amount of piretanide is 1.8-3.0% w/w,
(b) 65-85% w/w calcium sulphate dihydrate,
(c) 3.0-5.0% w/w sodium hydrogen carbonate,
(d) 10-20% w/w starch pregelatinised, and
(e) 0.5-1.5% w/w sodium stearyl fumarate.

8. The tablet formulation of claim 5, further comprising a diuretic.

9. The tablet formulation of claim 8, wherein the diuretic is hydrochlorothiazide.

10. The tablet formulation of claim 8, wherein the diuretic is piretanide.

11. The tablet formulation of claim 1, consisting essentially of:
a) 1.25 mg ramipril, wherein the amount of ramipril is 0.5-1.5% w/w,
b) 85-90% w/w of calcium sulphate dihydrate,
c) 0.5-1.5% w/w of sodium hydrogen carbonate,
d) 7-13% w/w starch pregelatinised, and
e) 0.5-1.5% w/w sodium stearyl fumarate.

12. The tablet formulation of claim 5, consisting essentially of:
(a) 2.5 mg, 5 mg or 10 mg ramipril, wherein the amount of ramipril is 1.4-2.5% w/w,
(b) 78-95% w/w calcium sulphate dihydrate,
(c) 1.4-2.5% w/w sodium hydrogen carbonate,
(d) 7-13% w/w starch pregelatinised, and
(e) 0.5-1.5% w/w sodium stearyl fumarate.

13. The tablet formulation of claim 6, consisting essentially of:
(a) 2.5 mg ramipril/12.5 mg hydrochlorothiazide or 5 mg ramipril/25 mg hydrochlorothiazide, wherein the amount of ramipril is 1.4-2.5% w/w,
(b) 8.5-10.5% w/w hydrochlorothiazide,
(c) 65-75% w/w calcium sulphate dihydrate,
(d) 1.0-2.5% w/w sodium hydrogen carbonate,
(e) 12-18% w/w starch pregelatinised, and
(f) 0.5-1.5% w/w sodium stearyl fumarate.

14. The tablet formulation of claim 7, consisting essentially of:
(a) 5 mg ramipril and 6 mg piretanide, wherein the amount of ramipril is 1.5-2.5% w/w and the amount of piretanide is 1.8-3.0% w/w,
(b) 65-85% w/w calcium sulphate dihydrate,
(c) 3.0-5.0% w/w sodium hydrogen carbonate,
(d) 10-20% w/w starch pregelatinised, and
(e) 0.5-1.5% w/w sodium stearyl fumarate.

* * * * *